(12) United States Patent
Fischer (10) Patent No.: US 7,906,076 B2
(45) Date of Patent: Mar. 15, 2011

(54) METHOD AND APPARATUS FOR BIOPSY SAMPLE PROCESSING

(75) Inventor: Andrew H. Fischer, Stow, MA (US)

(73) Assignee: University of Massachusetts, Boston, MA (US)

( * ) Notice: Subject to any disclaimer, the term of this patent is extended or adjusted under 35 U.S.C. 154(b) by 803 days.

(21) Appl. No.: 11/772,472

(22) Filed: Jul. 2, 2007

(65) Prior Publication Data

US 2009/0011399 A1   Jan. 8, 2009

(51) Int. Cl.
*B01L 3/00*   (2006.01)
(52) U.S. Cl. ......... 422/102; 422/100; 206/730; 206/733; 206/486; 206/564; 206/565; 600/562; 600/564
(58) Field of Classification Search .................. 422/102, 422/100; 206/730, 733, 486, 564, 565; 600/562, 600/564
See application file for complete search history.

(56) References Cited

U.S. PATENT DOCUMENTS

| | | |
|---|---|---|
| 2,923,669 A | 2/1960 | Poitra |
| 3,227,130 A | 1/1966 | Weiskoff |
| 4,141,312 A | 2/1979 | Louder et al. |
| 4,557,903 A | 12/1985 | McCormick |
| 4,569,647 A | 2/1986 | McCormick |
| 4,604,964 A | 8/1986 | Gordon et al. |
| 4,678,559 A | 7/1987 | Szabados |
| 4,801,553 A | 1/1989 | Owen et al. |
| 5,061,452 A | 10/1991 | Yamamoto et al. |
| 5,080,869 A | 1/1992 | McCormick |
| 5,137,710 A | 8/1992 | Smalley et al. |
| 5,185,084 A | 2/1993 | Lapidus et al. |
| 5,234,585 A | 8/1993 | Zuk, Jr. |
| 5,266,495 A | 11/1993 | Lapidus |
| 5,269,671 A | 12/1993 | McCormick |
| 5,312,758 A | 5/1994 | Ahlqvist |
| 5,354,370 A | 10/1994 | Schmehl |
| 5,424,040 A | 6/1995 | Bjornsson |
| 5,427,742 A | 6/1995 | Holland |
| 5,665,398 A | 9/1997 | McCormick |
| 5,667,985 A | 9/1997 | O'Leary et al. |
| 5,691,633 A | 11/1997 | Liu et al. |
| 5,817,032 A | 10/1998 | Williamson, IV et al. |
| 5,843,700 A | 12/1998 | Kerrod et al. |

(Continued)

FOREIGN PATENT DOCUMENTS

EP   0 245 969 A2   11/1987

(Continued)

OTHER PUBLICATIONS

Diaz-Rosario L. et al., "Cell Block Preparation by Inverted Filter Sedimentation is Useful in the Differential Diagnosis of Atypical Glandular Cells of Undetermined Significance in ThinPrep Specimens," CANCER Cytopathology, American Cancer Society, 2000, pp. 265-272.

(Continued)

*Primary Examiner* — Brian J Sines
(74) *Attorney, Agent, or Firm* — Wolf, Greenfield & Sacks, P.C.

(57) ABSTRACT

A container for use in processing a biopsy sample. Biopsy sample and materials are received within a sample processing area of the container. A semi-permeable barrier is positioned at a downstream portion of the sample processing area and prevents the prevent passage of the biopsy sample. A cap is positioned at the downstream side of the barrier, and holds fluids within the container.

17 Claims, 4 Drawing Sheets

U.S. PATENT DOCUMENTS

| | | |
|---|---|---|
| 5,928,934 A | 7/1999 | McCormick |
| 6,017,476 A | 1/2000 | Renshaw |
| 6,042,874 A | 3/2000 | Visinoni et al. |
| 6,207,408 B1 | 3/2001 | Essenfeld et al. |
| 6,395,234 B1 | 5/2002 | Hunnell et al. |
| 6,413,767 B1 | 7/2002 | Izvoztchikov et al. |
| 6,883,958 B2 | 4/2005 | Mayer |
| 6,899,850 B2 | 5/2005 | Haywood et al. |
| 6,905,594 B2 | 6/2005 | Ferguson |
| 6,913,921 B2 | 7/2005 | Fischer |
| 7,005,110 B2 | 2/2006 | Taft et al. |
| 7,147,826 B2 | 12/2006 | Haywood et al. |
| 7,156,814 B1 | 1/2007 | Williamson, IV et al. |
| 2005/0247646 A1 | 11/2005 | Linder |
| 2006/0088930 A1 | 4/2006 | Smith et al. |
| 2008/0057573 A1 | 3/2008 | Hutchins et al. |
| 2008/0081351 A1 | 4/2008 | Hutchins et al. |
| 2008/0081363 A1 | 4/2008 | Hutchins et al. |

FOREIGN PATENT DOCUMENTS

| | | |
|---|---|---|
| GB | 2278441 A | 11/1994 |
| WO | WO 91/03720 A1 | 3/1991 |
| WO | WO 95/14221 A1 | 5/1995 |
| WO | WO 00/19897 A1 | 4/2000 |
| WO | WO0067639 A1 | 11/2000 |
| WO | WO 2006/060317 A1 | 6/2006 |
| WO | WO2006/096581 A1 | 9/2006 |

OTHER PUBLICATIONS

Fahey C. et al., "Collodion Bag: A Cell Block Technique for Enhanced Cell Collection," Histology, Laboratory Medicine, vol. 74, No. 2, Feb. 1993, pp. 94-96.

Srinivasan, M. et al., "Effect of Fixatives and Tissue Processing on the Content and Integrity of Nucleic Acids," Review, American Journal of Pathology, vol. 161, No. 6, Dec. 2002, pp. 1961-1971.

Yang, G. et al., "Compact Cell Block, Use of Body Fluids, Fine Needle Aspirations and Endometrial Brush Biopsies," Acta-Cytologica, 1997, pp. 703-706.

METHOD AND APPARATUS FOR BIOPSY SAMPLE PROCESSING

BACKGROUND

1. Field

The present invention relates to a container and method for processing biopsy samples, and more particularly to a container and method for embedding biopsy samples for subsequent cross-sectioning.

2. Discussion of Related Art

Biopsy samples are often sliced into thin sections (e.g., 2 to 25 micron thick sections), such as by a microtome, prior to being analyzed. Sectioning a sample in this regard may help a medical professional in making an assessment under a microscope, such as to diagnose relationships among cells and other constituents of the biopsy sample. Sectioned samples may also be used to help analyze the molecular composition of a biopsy.

Prior to sectioning, processing of a biopsy sample typically includes several steps that lead to the sample becoming embedded within a solid substrate. One such common solid substrate is paraffin wax, which holds the sample in position and provides a uniform consistency to facilitate sectioning by the microtome. The method of processing the sample into the embedding substrate may include one or more of the following steps: 1—Fixation to immobilize the molecular components of a biopsy sample and/or prevent sample degradation. 2-Transferring the sample from a biopsy container to a processing cassette. 3-Infiltrating the sample with an embedding material, such as paraffin wax. 4-Embedding the sample. The step of infiltrating the cells of the biopsy sample typically involves first exposing the sample to alcohol to remove water from the sample, then exposing the sample to xylene to remove the alcohol and fatty substances. Liquid wax is then applied to wash away the xylene and fill the sample with paraffin to "infiltrate" all of the spaces that were originally filled with water or fatty substances. The step of embedding the sample involves positioning the tissue within a liquid embedding material. The paraffin wax is cooled to harden, immobilizing the tissue for later sectioning.

Existing practices for fixing, transferring, infiltrating, and embedding a biopsy sample typically involve manual handling. Such transfer steps may increase the likelihood of misidentifying a sample, contaminating a sample with part of another patient's sample, or losing part of, or even all of, the sample. Moreover, the numerous steps may increase the time that it takes to provide an assessment for a sample, once the sample has been collected from a patient. Existing practices also pose difficulties in positioning samples in a common plane for sectioning, particularly when there are multiple samples or sample fragments being embedded together.

SUMMARY

According to one aspect, a container for use in processing a biopsy sample is disclosed. The container comprises a first chamber for receiving a biopsy sample. A semi-permeable barrier is located at a downstream portion of the first chamber. The semi-permeable barrier is configured to prevent passage of the biopsy sample. A second chamber is positioned to receive material that passes from the first chamber and through the semi-permeable barrier. At least a portion of the second chamber includes a selectively accessible portion that allows material to exit the second chamber when accessed.

According to another aspect, a combination of a container for processing a biopsy sample and embedding material is disclosed. The container of the combination comprises a first chamber configured to receive a biopsy sample and embedding material. The first chamber includes a sample processing area. A semi-permeable barrier is positioned at a downstream portion of the sample processing area and is configured to prevent passage of the biopsy sample. The embedding material of the combination comprises a bolus of solid embedding material. The bolus is sized to fit within the sample processing area adjacent to the semi-permeable barrier.

According to still another aspect, a container for use in processing a biopsy sample is disclosed that comprises a first chamber for receiving a biopsy sample and at least one material to process the biopsy sample. The first chamber includes a sample processing area with a substantially oval cross-section. A semi-permeable barrier is at a downstream portion of the first chamber and is configured to prevent passage of the biopsy sample. The semi-permeable barrier comprises a filter medium and a thermally conductive filter media support structure. A second chamber is positioned to receive material that passes from the first chamber and through the semi-permeable barrier. The second chamber defines a space capable of sustaining a reduced pressure that, when present in the space, urges material and the sample in the first chamber toward the semi-permeable barrier. A cap defines at least a portion of the second chamber and includes a rubber material or valve that, when pierced or the valve is opened, allows material to be drawn from the second chamber. The semi-permeable barrier is coupled to the cap such that when the cap is separated from the container, the semi-permeable barrier is also separated from the container leaving the embedded biopsy sample at the downstream portion protruding from a portion of the first chamber.

According to yet another aspect, a method of processing a biopsy sample is disclosed. The method comprises providing a container that includes a first chamber to hold a biopsy sample and material to process the biopsy sample. The container has a semi-permeable barrier that prevents passage of the biopsy sample from the first chamber. The method also discloses selectively accessing a portion of the container to allow the material to move from the first chamber, through a semi-permeable barrier, and out of the container.

According to still another aspect, a method of embedding a biopsy sample is disclosed that comprises placing a biopsy sample into a sample processing area of a container. The method also comprises positioning a bolus of solid wax into the sample processing area above the sample.

BRIEF DESCRIPTION OF DRAWINGS

Various embodiments of the invention will now be described, by way of example, with reference to the accompanying drawings, in which.

DETAILED DESCRIPTION

Aspects of the present invention relate to a container suitable for processing a biopsy sample. According to some embodiments, the container is configured to receive a biopsy sample and to provide a sample processing area for fixation, infiltration, and/or embedding of the biopsy sample. In this respect, embodiments of the container may simplify the manner in which biopsy samples are processed.

The container is accessible such as through a pierceable material that, when accessed, may allow fluid to exit the container. The piercable material may be suited to receive a hollow needle, which may be used to draw air and/or fluid from the container so as to urge the biopsy sample, infiltrating materials, and/or embedding materials through a sample processing area and toward a semi-permeable barrier.

Aspects of the present invention also relate to a bolus of solid embedding material, such as paraffin wax, that may be inserted into the sample processing area of a container. The bolus of wax may help position one or more samples or sample fragments appropriately for embedding and later cross-sectioning. According to some embodiments, the bolus of wax may be shaped and sized to conform to an inner surface of the sample processing area in the container. In this respect, contact between the bolus and walls of the sample processing area may help direct sample and/or residual material from the walls and toward a downstream portion of the sample processing area.

Figure 1:
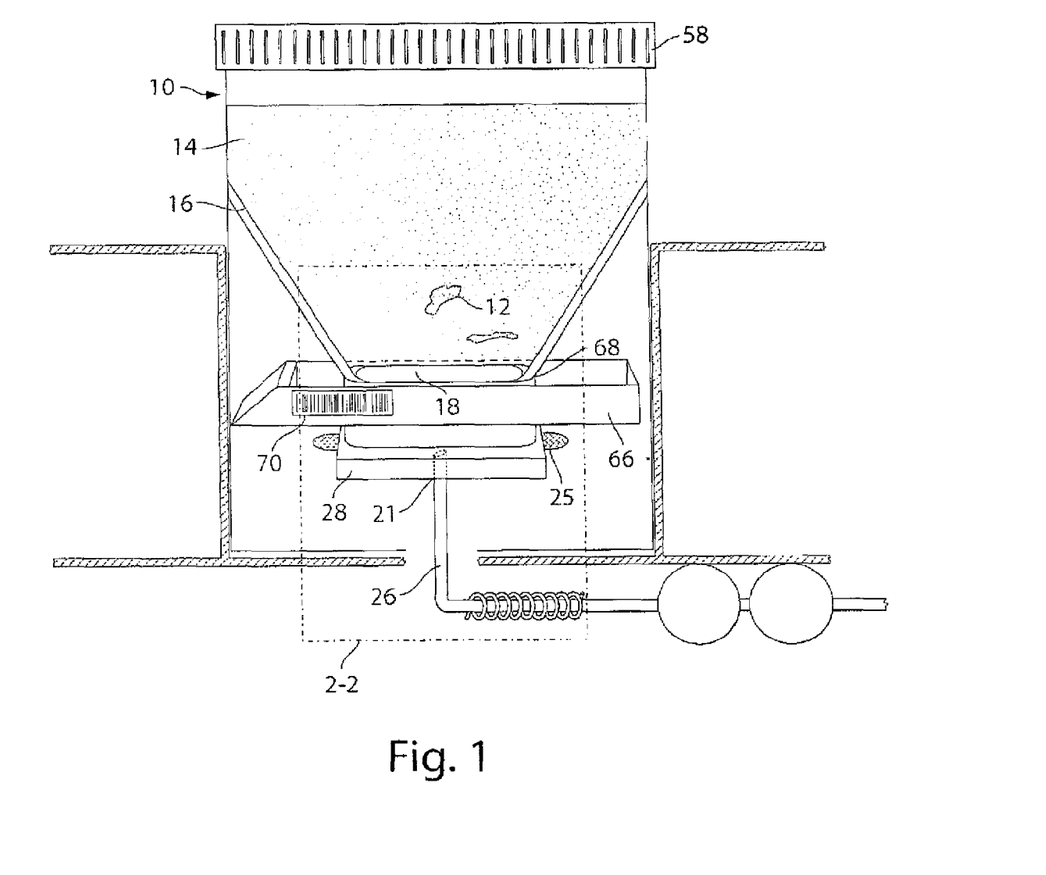
FIG. 1 is a perspective view of a container for processing a biopsy sample, according to one embodiment.
Figure 2:
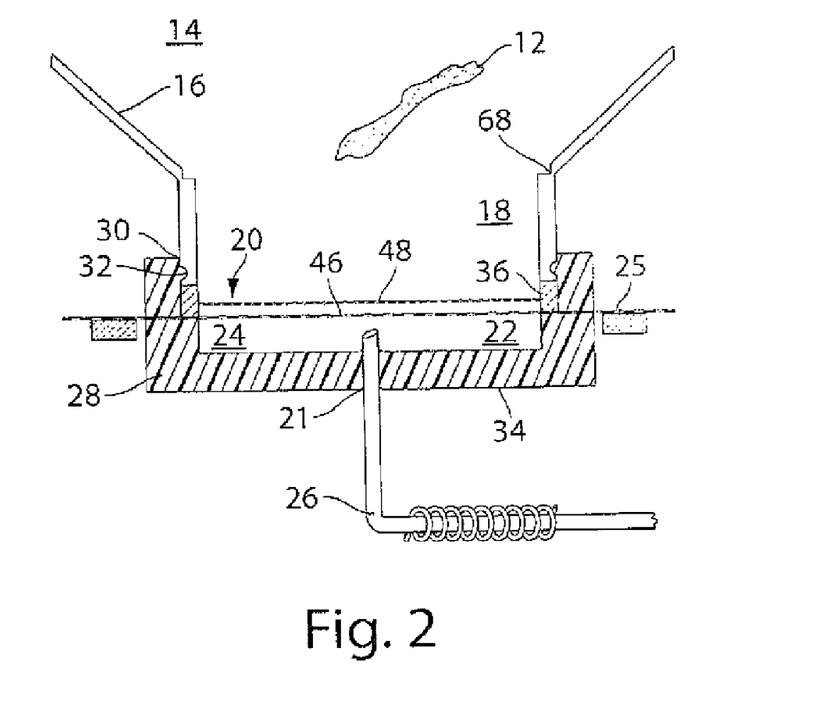
FIG. 2 is a cross-sectional view of the container shown in FIG. 1, taken along plane 2-2 and showing a hollow needle inserted into the sealing cap.

Turning now to the figures, and initially FIGS. 1 and 2, which show a container 10 that may be used to process a biopsy sample 12 (FIG. 2 is a view of the embodiment shown in FIG. 1, taken about plane 2-2). The container includes a first chamber 14 in which sample and processing materials may be received. A funnel shaped portion 16 may be included to facilitate reception of the sample and materials into the first chamber and also to direct the sample and materials to a sample processing area 18 and a semi-permeable barrier 20 located at a downstream portion of the processing area. A cap 28 is located at a downstream side of the semi-permeable barrier and may seal the container such that materials may be retained therein. The cap may also define a second chamber 22 that may be configured to receive the end of a needle 26, or in which fluids may be received and/or contained, although according to some embodiments, the cap may lie directly adjacent to the semi-permeable barrier, such that the second chamber is very small. Portions of the second chamber, such as the cap, may include a selectively accessible port 21, such as piercable material that, when pierced, allows fluids to exit the container.

According to some embodiments, the second chamber defines a space 24 from which air and/or fluid may be drawn so as to create a reduced pressure. This reduced pressure, in turn, draws the sample and materials toward the semi-permeable barrier. In the embodiment of FIG. 1, the second chamber is configured to receive a needle that draws air and/or fluid from the second chamber to create the reduced pressure. Although the embodiment of FIGS. 1 and 2 uses a reduced pressure in the second chamber to draw materials toward and/or through the barrier, it is to be appreciated that in other embodiments, an increased pressure applied on the upstream side (i.e., first chamber side) of the barrier may also be used to force fluids or material toward the barrier 20. Still, according to other embodiments, piercing the second chamber simply allows fluid materials resident in the second chamber to escape, thus allowing flow through the sample processing area.

The container may include a removable sealing cap 28 that defines the second chamber, at least in part. By way of example, FIG. 2 shows the second chamber and the interface between the cap and the container. The cap, as illustrated, is made of a compliant material, like an elastomeric material, that may be stretched slightly to engage the lower portion of the sample processing area. As shown, the lower, outer wall 30 of the sample processing area includes a recessed feature 32 that engages a corresponding protrusion on the cap to help hold the cap in place. In other embodiments, the cap may comprise a more rigid material, like plastic, and may engage the container in a different manner, such as with a threaded joint or other types of interfaces.

As discussed above, the second chamber may be configured to sustain a reduced pressure, at least temporarily, so that contents of the first chamber may be urged toward the barrier or may be held at the barrier. To help accomplish this, the second chamber may be sealed from the ambient environment, except at the semi-permeable barrier and at an outlet in the second chamber from which air and/or fluids are drawn. In the embodiment of FIGS. 1 and 2, the cap is made of rubber that is stretched slightly about the lower end of the sample processing area to help create a seal. Other features, such as separate seals, may be used in place of or in combination with such a compliant cap. As constructed, the embodiment of FIGS. 1 and 2 prevents the intrusion of air at points other than the barrier so that a pressure less than ambient may be created.

Air and/or fluids may exit the second chamber in various ways to allow fluids to flow through the processing area of the container. In the embodiment of FIGS. 1 and 2, the cap may be pierced by a hollow needle to provide an outlet for air and/or fluid that resides in the container. Fluids may then flow freely from the container through the needle. According to some embodiments, the needle may be connected to a pump of a sample processing machine that draws air/fluid from the container. The outer surface of the needle may form a seal against the rubber material of the cap to prevent air and/or fluid leaks. According to other embodiments, the piercable cap may be replaced by other types of selectively accessible ports, such as a port with a valve that is opened when the port is connected to a device. It is to be appreciated that the term "piercable", as used herein refers to a material or structure that may be penetrated by a typical needle to provide a passageway through the material.

In the embodiment of FIGS. 1 and 2, the rubber material that receives the hollow needle is solid in construction, lacking slits or score marks to receive the needle, although other embodiments may include such features. Moreover, although the embodiment of FIGS. 1 and 2 has a rubber material that is to be pierced by a hollow needle, other compliant materials may also be used, particularly those that allow a needle to pass while also sealing against lateral surfaces of the needle.

The outlet from the second chamber may be positioned at various places. In the embodiment of FIGS. 1 and 2, a bottom surface 34 of the second chamber is configured to be pierced by the hollow needle. This configuration may allow automatic piercing to occur by an upwardly oriented needle when the container is placed downward onto a sample processing machine, as is discussed herein in greater detail. However, the rubber cap shown in FIGS. 1 and 2 may also be pierced at other positions, such as at lateral sides of the cap, or any other position that provides access to the space in the second chamber.

Embodiments may be configured such that the semi-permeable barrier is removed from the container along with the cap. In this respect, the steps of removing the cap and then removing the barrier may be consolidated to simplify use. This is accomplished in the embodiment of FIGS. 1 and 2 by sandwiching the semi-permeable barrier between a spacer ring 36 and the cap. The spacer ring is held to the cap with a stronger force, such as from interference between the cap and spacer ring, than that present between the cap and the container. In this respect, when the force between the cap and container is overcome to remove the cap, the spacer ring and barrier may follow the cap rather than remaining present on the lower portion of the sample processing area. Once the cap is removed from the container, the spacer ring and barrier may then be removed from the cap, if desired. In other embodiments, the cap may be permanently attached to or integral with the barrier and/or the spacer ring, as it is to be appreciated that they need not be removable from one another in all embodiments.

Figure 3:
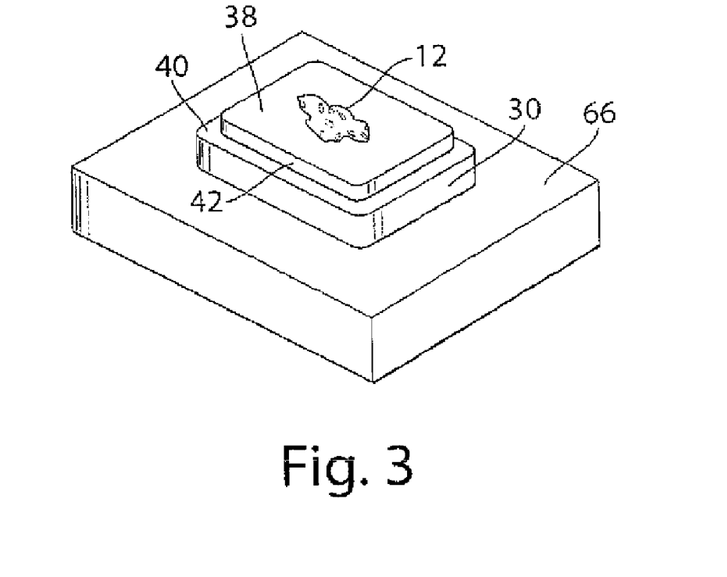
FIG. 3 is a perspective view of an embedded sample.

The container may include features to leave a portion of the embedded biopsy sample protruding from the sample processing area for sectioning, as shown in FIG. 3. Here, the wax 38 and embedded sample 12 extend for a distance, thereby providing access to sides 42 of the embedded sample for a microtome blade or other sectioning device. This protrusion is created in the embodiment of FIG. 2 by removing the spacer ring that is positioned around the upstream side of the barrier in the sample processing area. The protrusion of the embedded wax sample may extend for different distances, based on the configuration of the container and spacer ring. According to some embodiments, the protrusion may extend for up to 1 millimeter, up to 2 millimeters, up to 5 millimeters, or even greater.

The spacer ring and/or other components, such as the cap 28, that are removed to expose the embedded sample may have features that promote clean separation from the wax or other embedding material. For instance, the spacer ring may be made of a material, such as polyester, that has been found to be cleanly separable from hardened wax. That is, typically only small amounts of wax, if any, remain adhered to the spacer ring when removed. The surface finish of the spacer ring, and/or other components, may also be relatively smooth to promote a clean separation.

Features may be incorporated into the sample processing area to hold the embedding material and sample in place as the barrier is removed. By way of example, the lower inner surface of the sample processing area could be composed of a plastic with embedded glass or talc particles that have been found to adhere to solidified paraffin. Adherence of the embedding medium to the inner surface of the sample processing area can also be achieved in other ways, such as by having a thin shelf-like protuberance that prevents the hardened embedding material from pulling away from the cassette.

Embodiments of the container may include different constructions of semi-permeable barriers. In the illustrated embodiment, the barrier comprises both a filter support 46 and filter media 48. The filter support may help hold the filter media in place as the sample is processed. This can, in turn, provide better control over the shape and positioning of the wax in which the biopsy sample is embedded. In the embodiment of FIGS. 1 and 2, the filter support includes a screen that extends across a downstream portion of the sample processing area. The screen has openings that are large enough to allow the free passage of fluids and some samples, yet small enough and stiff enough to hold a filter medium in position against any pressure/vacuum force or pushing by a bolus of solid embedding material. Various embodiments of the screen may have pores that range in size from about 0.01 millimeters to about 5 millimeters across, and are generally larger in size than pores of the filter medium.

The barrier of the illustrated embodiment also includes filter medium that is positioned on the upstream side of the filter support. The filter medium may be made of various materials, including polycarbonate and polyester, among others. The filter may have a generally smooth surface and be constructed of a material, such as polyester, that resists sticking to paraffin. The average pore size is typically greater than 1 microns and less than 250 microns, although aspects of the invention are not limited to any one particular construction or size of filter media. Filter media having a pore size of about 100 microns has been found to reduce the likelihood of clogging during use and may be purchased from Small Parts, Inc. under product number CMY-0105-D. Larger pore sizes, such as 250 micron pores, may prove beneficial for certain biopsy types. Although the illustrated embodiment has a semi-permeable barrier that comprises a filter support and a separate filter medium, it is to be appreciated that other embodiments may have a barrier that is constructed differently. According to one embodiment, the barrier consists of a single component that is self supported and that has pores of a size needed to provide adequate filtering.

Various techniques may be used to improve the smoothness of filter medium, causing it to have lower adherence to paraffin or other embedding media. According to one embodiment, filter media made of woven polyester material can be made more smooth by pressing the medium between heated smooth rollers.

Embodiments of the container may include features that promote heating of materials in the sample processing area. By way of example, the filter support of the embodiment shown in FIG. 2, may be made of a metal or mesh screen, and may include conductive material, like brass, aluminum, and the like. This filter support may be placed in contact with or proximity to a heater, such as when the container is positioned in a sample processing machine. According to some embodiments, a conductive filter support 46 extends through the sealing cap to make contact with a heater 25, thus providing a thermally conductive pathway for heat to enter the sample processing area from outside of the container. Heat applied to the filter support may promote melting of wax that lies upstream from the barrier to help embed the biopsy sample. It is to be appreciated that other components of the container may also be thermally conductive to promote heating, such as the spacer, the cap, and or portions of the sample processing area itself.

Embodiments may also include features to heat the second chamber, or other portions of the container. For instance, the hollow needle that pierces the cap of the container may itself be heated. The heated needle can help heat and melt wax passing through the sample processing area. Moreover, the heated needle may help prevent wax or other materials from solidifying in the second chamber or in the needle itself, which might otherwise cause clogging in the system.

Various embodiments of the container may include features to direct biopsy samples and materials toward the sample processing area and/or the semi-permeable barrier or to hold such samples and/or materials at the barrier. In the embodiment of FIGS. 1 and 2, an upper portion of the first chamber is funnel-shaped, such that biopsy samples and other materials, whether liquid or solid, may be directed to the sample processing area. The shape may also allow fluids, such as those provided from a manually operated pipette or an automated sample processing machine, to be washed over the entire surface of the funnel to direct any residual solids or liquids into the sample processing area. For example, in FIG. 5, the reagent delivery arm 63 may move in a circular path to expel reagents around the full circumference of the funnel-shaped collection area 16 and thereby tend to urge all fragments that may have settled onto the funnel shaped collection area 16 to wash into the sample processing area 18.

Various embodiments may include features to help position biopsy particle(s) in a plane that lies adjacent to the semi-permeable barrier. According to some embodiments, a bolus 54 of solid embedding material, such as paraffin wax, may be used to position the sample and/or materials about the sample processing area and/or in a plane that lies adjacent to the semi-permeable barrier. In this respect, the sample may be positioned appropriately by the bolus for later sectioning by a microtome. Such a bolus may prove particularly beneficial for samples that comprise numerous, relatively small fragments. It is to be appreciated that the term "bolus" as used herein, defines a lump of solid material that may have a rounded shape, a partially rounded shape, or even an angular, rectangular like shape.

Figure 4:
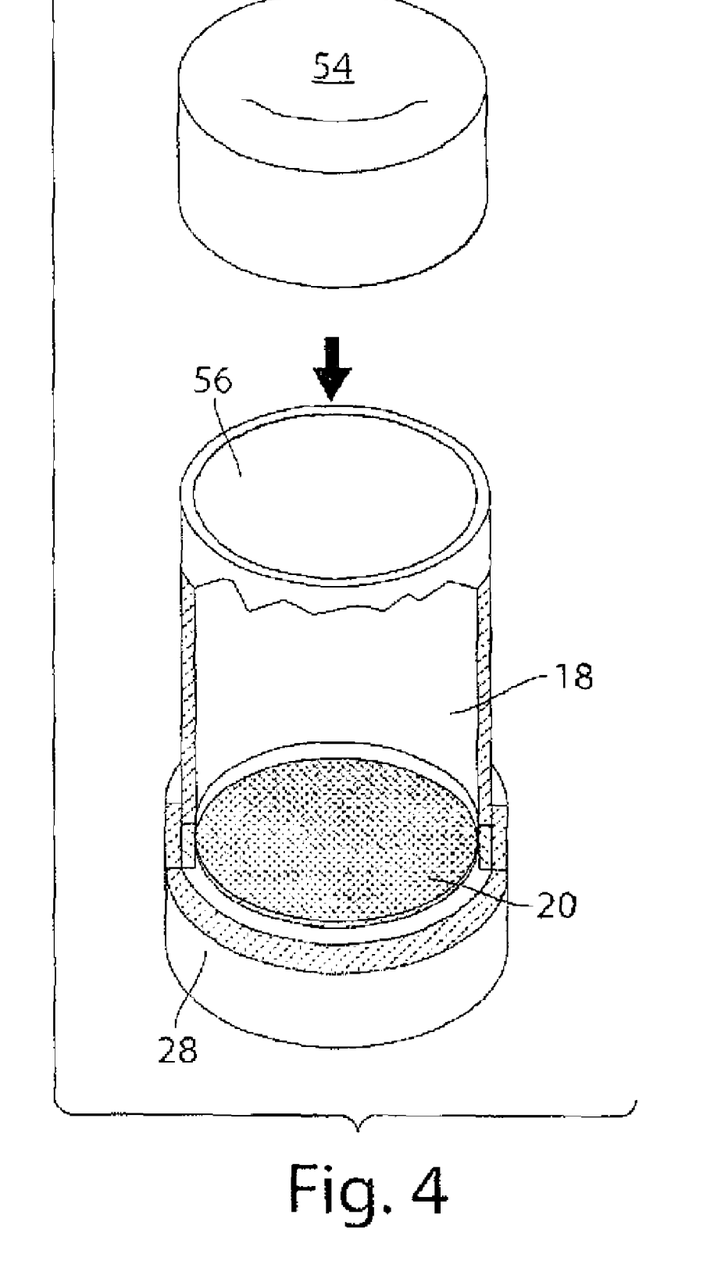
FIG. 4 is a view of a solid bolus of embedding material placed into a sample processing area of a container, according to one embodiment.

The embodiment shown in FIG. 4 includes a bolus of solid paraffin wax, that is shaped with lateral sides that conform substantially to the inner surfaces 56 of the sample processing area. When inserted into the sample processing area, the bolus may be urged downward through the sample processing area until a substantially planar lower surface of the bolus is holding or pressing the sample against the semi-permeable barrier. The sample may thus be held close to the plane defined by the semi-permeable barrier while the paraffin-embedded sample solidifies.

According to some embodiments the bolus of solid embedding material may be heated to improve bonding with an infiltrated biopsy sample. In this respect, the material of the bolus and the material of the infiltrated sample may harden together, thereby providing a structure that is more structurally stable for sectioning. Various techniques may be used to heat the bolus. According to some embodiments, the bolus is solid material may be positioned adjacent to an open flame or a heated solid surface such that the surface that lies adjacent to the semi-permeable barrier is at least partially melted prior to being inserted into the sample processing area. According to other embodiments, the bolus of solid material is heated after it has been introduced to the sample processing area and lies adjacent to the sample. This may be accomplished by a thermally conductive barrier, like that described herein.

It is to be appreciated that a uniform bonding of the paraffin may also be achieved after the biopsy sample has become appropriately positioned and embedded. Remelting a portion of the embedded material and sample may promote uniform bonding of the biopsy sample with the paraffin. In such approaches, it may prove advantageous to simply heat an area of the solidified embedding material that lies adjacent to the sample, such that the distance that the sample may move is minimized.

The bolus of embedding material can also be used to provide a sufficient quantity of embedding material to effect the infiltration step of sample processing. For example, after a sample has been processed through the xylene extraction, a bolus of solid paraffin wax can push any residual xylene and biopsy sample that may be adhered to the surface of the sample processing area 18 toward the filter 48. The filter support 46 may then be heated, such that the solid bolus of wax will melt adjacent to the sample. Application of pressure on the bolus and/or vacuum within the second chamber while heating may help urge additional molten wax to flow through the sample to effect a complete paraffin infiltration.

The bolus of wax may provide all of the wax needed to embed a sample, or may be used in conjunction with other wax that is provided to the sample processing area. For embodiments where additional molten wax is provided to the sample processing area, the bolus may include features that allow passage of the molten wax. For instance, according to some embodiments, grooves or passageways may be present around the periphery of the bolus. Still, according to other embodiments, passageways may extend through central portions of the bolus to allow molten wax provided on top of the bolus to pass there through and to reach a sample that is being embedded. In other embodiments, the bolus may simply be much smaller in cross-sectional size than the sample processing area, such that other processing fluids may freely pass between the bolus and walls of the sample processing area.

According to some embodiments, the bolus of wax may be shaped to have a cross-section that conforms with but is slightly smaller in size than the cross-section of the sample processing area. In such embodiments, the bolus may slide with minimal or no urging by an operator so that the bolus can move directly on top of a biopsy sample to help position the sample in the plane that lies adjacent to the semi-permeable barrier. In some of such embodiments, a gap of less than 0.1 millimeters is present between the bolus and the walls of the sample processing area, although larger gaps are possible, as aspects of the invention are not limited in this respect. The gap may be sized to control the amount of force that would be needed to displace the bolus, or to control the size of particles that may be advantageously allowed to move around the bolus.

According to other embodiments, the bolus of wax may conform in shape, but advantageously be slightly larger in size than the cross-section of the sample processing area. Such an "interference fit" may force all of the residual processing materials and any small-sized biopsy particles toward the semi-permeable barrier, maximizing the efficiency of the removal of processing reagents and maximizing recovery of biopsy particles at the plane of the semi-permeable membrane. An interference fit may also cause the bolus to be tightly adherent to the lower inner wall of the sample processing area, allowing the semi-permeable barrier, cap, and/or spacer ring to be removed from the infiltrated embedded sample and bonded bolus without detaching the embedded sample from the cassette itself.

According to some embodiments, the bolus has at least about 0.5 millimeters of interference with all points of the inner surface of the sample processing area. However, in other embodiments, the interference may be less, or even greater, such as up to 1 millimeter, up to 2 millimeters, or even greater, as aspects of the invention are not limited in this respect. Moreover, the interference between the bolus and the sample processing area need not be the same at all points about the perimeter of the sample processing area and in some embodiments, the bolus may have a tapered or otherwise non-constant cross-sectional shape such that the interference between the walls and the bolus varies from point to point.

It is to be appreciated that although the bolus of solid embedding material has been described herein as a bolus of paraffin wax, that other embedding materials may also be used. For instance, other sectionable materials such as an OCT compound and various water soluble plastics may also be used to embed biopsy samples and may also be formed as a bolus of solid material and placed in the sample processing area, according to some embodiments.

The bolus may comprise different volumes of wax, depending on the biopsy sample size and the size of the sample processing area. According to some embodiments, the bolus of wax has between 4 and 20 cubic centimeters of wax, although other volumes are possible. Moreover, the bolus may comprise materials other than paraffin wax and/or combinations of wax and other materials, as aspects of the invention are not limited in this respect.

The sample processing area may have different cross-sectional shapes. In the embodiment illustrated in FIGS. 1 and 2, the sample processing area defines an ovalized "race track" shape. Such a race track shape may offer several advantages:

First, the long straight line allows serial sections to "ribbon" (stick together side-by-side) when cut with the long axis parallel to the microtome blade. Sectioning in this plane may allow relatively more sections to be placed on a microscope slide compared to having the same area of fragments embedded within a circular area. Additionally, the oval race-track shape may better accommodate core biopsies, a commonly shaped biopsy type. In one embodiment, the long axis of the oval area is about 24 mm (less than the width of a standard microscope slide) and the short axis is about 10 mm. The sample processing area may also have substantially the same cross-sectional shape and size from the upstream portion to the downstream portion. In other illustrative embodiments, the sample processing area is shown to have a more circular cross-sectional shape. It is to be appreciated, however, that other shapes and configurations are also possible, such as sample processing areas that taper from top to bottom, or that have different cross-sectional shapes.

Embodiments of the container include features to streamline the process of embedding biopsy samples. According to some embodiments, the container is configured to receive a biopsy sample immediately after the sample is harvested from a subject, and to retain the biopsy sample until the sample has been embedded, ready to be sectioned by a microtome. In this respect, embodiments of the container with such features may be considered "integrated."

Integrated containers may have a shape that is readily grasped and surely held by healthcare professionals, such as during sample collection or simply while handling the container. The embodiment illustrated in FIG. 1 has a generally cylindrical shape that helps accomplish this effect. The container also includes a screw on lid 58 that may be readily taken on or off during sample collection and/or processing. The sealing cap of the second chamber is recessed within the outer envelope of the container, which may help protect the cap from inadvertent damage and may help prevent contamination. The recess in the bottom of the container may also promote stacking with other containers during shipping and/or storage.

The container may have a shape that conforms to a receptacle in a sample processing machine. By way of example, the sample processing machine 60 shown in FIG. 5 includes a generally cylindrical receptacle 62 in which a container may be received. As shown, the receptacle includes a flat side 64 that engages a corresponding cut out of the container. Engagement between these features can help orient the container properly to the machine. Additionally, this engagement may prevent unwanted rotation of the container within the receptacle, such as might otherwise occur when the lid is removed in an automated or manual fashion. It is to be appreciated that other features may be used to engage the container to the sample processing machine, as aspects of the invention are not limited to those shown in the figures.

The container may be configured to automatically place the first or second chamber in fluid communication with the machine when the container is positioned in the receptacle. The machine illustrated in FIG. 5 includes a hollow needle (not shown) that points upwardly from a bottom surface of the receptacle in the machine. The needle pierces the pliable material of the cap to automatically provide fluid communication between the machine and second chamber when the container is seated in the receptacle. In this respect, the construction of the sample processing machine may be simplified, and the number of steps required for processing the sample may be reduced. It is to be appreciated, however, that other embodiments are possible, including embodiments that do not automatically provide fluid communication between the second chamber and the machine when the container is inserted therein.

Embodiments of the integrated container may also incorporate a rectangular cassette 66 of the type accepted by many microtome devices. As shown in FIG. 1, the cassette may be positioned about the sample processing area such that the sample, when embedded, lies in a central portion of the cassette. The illustrated cassette is substantially rectangular in shape.

Embodiments of integrated containers may include features that allow the cassette to be separated from the container, so that the cassette may be readily placed in a microtome or other device for sectioning. By way of example, the joint between the cassette and the funnel shaped portion of the container, as shown in FIG. 1, may be scored 68, such that the cassette may be readily broken free from the remaining portions of the container. Other types of separable joints may also be used, such as threaded joints and the like.

Labels may be incorporated into some container embodiments so that samples may be tracked throughout sampling, processing, and sectioning. According to the embodiment shown in FIG. 1, the cassette includes a unique bar code 70 that may also be scribed onto the outer surface of the sample container. By providing two identical and unique bar codes, the bar code can become associated with a particular sample / patient during sample collection, and be used to maintain the identity of the sample through processing, and sectioning since the biopsy sample may stay with the sample container until the biopsy sample is embedded in the cassette. It is to be appreciated that identifiers other than bar codes may also be incorporated into the container, like RFID tags, or write-on surfaces, as aspects of the invention are not limited to bar codes, or even to having an identifier.

Typical use of the container shown in FIGS. 1 and 2 includes initially scanning the bar code label to associate the container with a particular patient. The lid of the container is then opened to receive a biopsy sample that has been harvested. Once the sample is collected, the lid is replaced and the container is transferred to the sample processing machine for processing. Fluids for preserving the sample may be added to the container after the sample is harvested or may be present in the container prior to sample collection.

Figure 5:
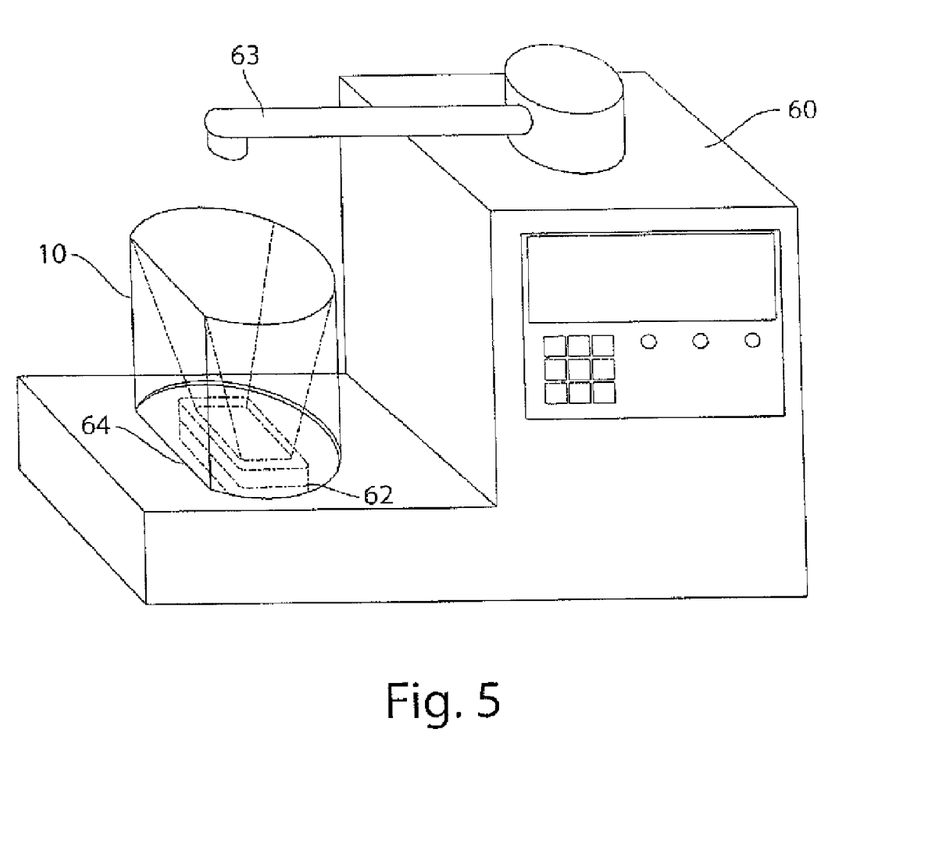
FIG. 5. is a perspective view of a sample processing machine with a container, like that shown in FIG. 1, loaded into a receptacle of the machine.

The container is inserted into the receptacle of the sample processing machine, which may allow the hollow needle of the machine to pierce the rubber cap of the container. The lid of the container is removed to allow air to enter the sample processing area and to provide access to the sample processing area from above for processing materials and a solid wax bolus. Although a single station with one container is illustrated in FIG. 5, it is to be appreciated that machines with multiple stations are also envisioned. Each station may have a piercing needle or valve that can independently apply suction or pressure to the second chamber, and which can be independently heated. Each station can have an independently operable Pelletier heater that makes thermal contact with a filter support and has a microprocessor that can apply heat or cold to the sample during specified times of the processing. A moveable robotic arm can deliver volumes of processing reagents to each of multiple processing stations. A fluid level monitor can be coupled to the arm to be used in conjunction with microprocessor-controlled application of vacuum to the second chamber such that reagents are pulled close to the semi-permeable barrier before adding additional fluids. According to some embodiments, multiple robotic arms and separate fluid level monitors may be used for a larger machine that can process large volumes (e.g., hundreds of samples at a time). After sufficient xylene has been passed through the sample to remove residual alcohol, the same or a different arm can deliver a solid bolus of paraffin to the sample processing area as previously described to effect the paraffin infiltration and embedding of the sample substantially at the plane above the semi-permeable barrier. According to some embodiments, the bolus is the sole source of wax provided to the sample. In other embodiments, molten wax is provided first to the sample processing area by a heated robot arm that may be separate from the robotic arm used in processing, and then the bolus of wax is added with provision for melting the lower surfaces of the bolus to enable bonding.

The container may be removed from the sample processing machine after the biopsy sample has been embedded in wax. The cassette may then be separated from the remaining portions of the container by bending the cassette relative to the remaining portions of the container. This may cause the container and cassette to separate at the score marks between the cassette and funnel portion of the first chamber.

The embedded sample may then be exposed for sectioning in a microtome by removing the cap from the sample processing area. As discussed herein, the semi-permeable barrier may be removed along with the cap to expose the embedded sample. With the embedded sample exposed, the cassette may be placed in a microtome or other device for sectioning. The bar code of the cassette could identify the sample embedded in the cassette and placed into the microtome.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. In combination, a container for processing a biopsy sample and an embedding material, the container of the combination comprising:
    a first chamber configured to receive a biopsy sample and embedding material, said first chamber including a sample processing area; and
    a semi-permeable barrier positioned at a downstream portion of said sample processing area, said semi-permeable barrier configured to prevent passage of the biopsy sample; and
    the embedding material of the combination comprising:
    a bolus of solid embedding material, said bolus being solid and sized to fit within said sample processing area adjacent to said semi-permeable barrier prior to insertion of said bolus into said sample processing area.

2. The combination of claim 1, wherein said sample processing area defines a cross-sectional shape and further wherein said bolus of embedding material is sized to fit within said cross-sectional shape without contacting walls of the sample processing area.

3. The combination of claim 2, wherein said bolus of embedding material is a oval-shaped mass of paraffin wax.

4. The combination of claim 1, wherein said sample processing area defines a cross-sectional shape and further wherein said bolus of embedding material has a shape that conforms to said cross-sectional shape.

5. The combination of claim 4, wherein said bolus is sized to have an interference fit with said cross-sectional shape of said sample processing area.

6. The combination of claim 4, wherein said bolus is sized substantially the same as said cross-section shape of said sample processing area.

7. The combination of claim 1, wherein said sample processing area defines a cross-sectional shape that is substantially constant from an upstream portion to a downstream portion of said sample processing area.

8. The combination of claim 1, wherein said sample processing area defines a substantially oval cross-sectional shape.

9. The combination of claim 2, wherein said first chamber comprises a funnel shaped portion that is located upstream of said sample processing area.

10. The combination of claim 1, wherein said sample processing area includes a locking feature to engage solidified material in which biopsy sample has been embedded.

11. The combination of claim 1, further comprising:
    a removable lid configured to close an upstream end of said sample processing area.

12. The combination of claim 1, wherein said sample processing area is incorporated into a cassette to be received by a microtome.

13. The combination of claim 12, wherein said cassette is removable from said container.

14. The combination of claim 1, further comprising:
    a second chamber that receives fluids that pass from said first chamber and through said semi-permeable barrier.

15. The combination of claim 1, further comprising:
    a cap that defines at least a portion of said second chamber, said cap being removable from said container.

16. The combination of claim 1, wherein said semi-permeable barrier has an average pore size between about 5 microns and about 250 microns.

17. The combination of claim 1, wherein said semi-permeable barrier has an average pore size of about 100 microns.

* * * * *